United States Patent [19]

Nakagawa et al.

[11] 4,284,628
[45] Aug. 18, 1981

[54] 2-HYDROXY BENZAMIDE DERIVATIVES AND USE THEREOF AS A FUNGICIDE

[75] Inventors: Taizo Nakagawa; Seiji Mochizuki, both of Ageo; Kaoru Ohmori, Okegawa; Kengo Koike, Ageo; Mineo Maruyama, Ageo; Eiichi Tanaka, Ageo, all of Japan

[73] Assignee: Nippon Kayaku Kabushiki Kaisha, Tokyo, Japan

[21] Appl. No.: 65,910

[22] Filed: Aug. 13, 1979

[30] Foreign Application Priority Data

Aug. 25, 1978 [JP] Japan .............................. 53-102789

[51] Int. Cl.³ .................... A01N 37/26; C07C 103/78
[52] U.S. Cl. ................................. 424/230; 260/454; 260/456 P; 260/463; 260/465 D; 560/42; 560/133; 560/138; 564/179
[58] Field of Search ............... 260/454, 463, 465 D, 260/456 P; 424/230; 560/42, 133, 138; 564/179

[56] References Cited

U.S. PATENT DOCUMENTS

| 3,644,518 | 2/1972 | Yoshida et al. | 260/559 S |
| 3,929,879 | 12/1975 | Taborsky | 260/559 S |
| 4,055,639 | 10/1977 | Hirose et al. | 424/230 |
| 4,200,632 | 4/1980 | Nakagawa et al. | 424/230 |

Primary Examiner—Richard Raymond
Attorney, Agent, or Firm—Russell & Nields

[57] ABSTRACT

A compound represented by the formula:

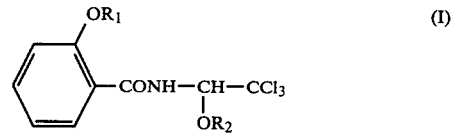

(I)

wherein $R_1$ is hydrogen, lower alkylcarbonyl, lower alkoxycarbonyl, phenoxycarbonyl, lower alkylsulfonyl or lower alkylcarbamoyl, $R_2$ is phenyl; phenyl substituted by one or more members selected from the group consisting of lower alkyl, lower alkoxy, lower alkylthio, lower alkoxycarbonyl, halogen, formyl, cyano, thiocyano, nitro, lower alkylsulfinyl, lower alkylsulfonyl, lower alkylcarbonyl, acetylamino or phenyl; or naphthyl, with the proviso that when $R_1$ is hydrogen or lower alkylcarbonyl, $R_2$ is the said substituted phenyl or naphthyl, and use thereof as a fungicide.

19 Claims, No Drawings

2-HYDROXY BENZAMIDE DERIVATIVES AND USE THEREOF AS A FUNGICIDE

DETAILED DESCRIPTION OF THE INVENTION

The present invention relates to new 2-hydroxybenzamide derivatives represented by the formula:

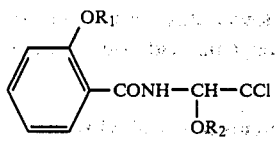

wherein $R_1$ is hydrogen, lower alkylcarbonyl, lower alkoxycarbonyl, phenoxycarbonyl, lower alkylsulfonyl or lower alkylcarbamoyl, $R_2$ is phenyl; phenyl substituted by one or more members selected from the group consisting of lower alkyl, lower alkoxy, lower alkylthio, lower alkoxycarbonyl, halogen, formyl, cyano, thiocyano, nitro, lower alkylsulfinyl, lower alkylsulfonyl, lower alkylcarbonyl, acetylamino or phenyl; or naphthyl, with the proviso that when $R_1$ is hydrogen or lower alkylcarbonyl, $R_2$ is the said substituted phenyl or naphthyl; a fungicidal composition for agriculture and horticulture comprising 0.5 to 95% by weight of said 2-hydroxybenzamide derivatives as effective components and a method of preventing fungi.

As fungicides used for protecting agricultural and horticultural plants from diseases, there have been used organomercurous compounds, organic chlorine compounds, organic phosphorous compounds and gaseous compounds. However, the organomercurous compounds have a very strong toxicity to humans and beasts. The organic chlorine compounds have a considerable phototoxity for plants. Since they are required in large amounts and in a high concentration for obtaining a satisfactory prevention effect, they are liable to remain in the plant body or in the soil. The gaseous fungicides have defects of irritative smell or bad smell.

After investigations for the development of agricultural and horticultural fungicides free of said defects, the inventors have found that compounds represented by formula (I) are highly effective in preventing agricultural and horticultural plants from diseases, particularly a remarkable effect against the clubroot of Cruciferous plants and rice blast disease with only a low concentration. The present invention has been attained on the basis of this finding.

The compounds of the present invention have only a very low toxicity to humans and beasts, do not damage plants, are free of irritative or unpleasant smell, and are capable of preventing diseases of plants in a low concentration. Therefore, the compounds can be used as ideal agricultural and horticultural fungicides in only a small amount without fear of soil contamination.

The terms "lower alkyl" and "lower alkoxy" herein designate alkyl and alkoxy groups having 1-6 carbon atoms, preferably such groups have 1-4 carbon atoms.

Preferred compounds of the present invention are compounds of formula (I) wherein $R_1$ is hydrogen and $R_2$ is substituted phenyl represented by the formula:

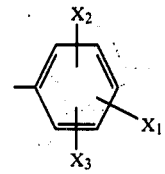

wherein $X_1$ is alkyl having 1-4 carbon atoms, methoxy, methoxycarbonyl, halogen, cyano, nitro, acetyl, thiocyano or phenyl, $X_2$ is hydrogen or alkyl having 1-3 carbon atoms and $X_3$ is hydrogen or methyl; or β-naphthyl.

More preferred compounds are:

(1) compounds represented by formula (I) wherein $R_1$ is hydrogen and $R_2$ is substituted phenyl represented by the formula:

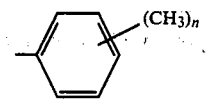

wherein n is an integer of 1–3;

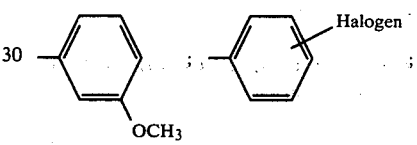

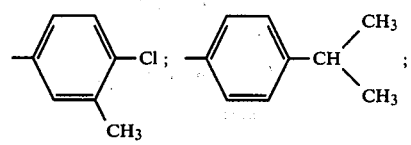

or β-naphthyl or (2) compounds represented by formula (I) wherein $R_1$ is acetyl and $R_2$ is substituted phenyl represented by the formula;

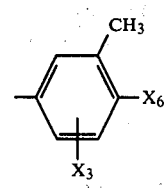

wherein $X_6$ is hydrogen, methylthio or chlorine and $X_3$ is hydrogen or methyl which is in m- or p-position to the methyl on the phenyl nucleus, with the proviso that when $X_3$ is methyl, $X_6$ is hydrogen; substituted phenyl represented by the formula:

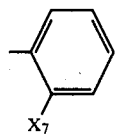

wherein $X_7$ is methyl, chlorine, acetyl or methoxy; substituted phenyl represented by the formula:

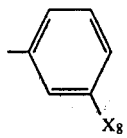

wherein X₈ is chlorine or fluorine; substituted phenyl represented by the formula:

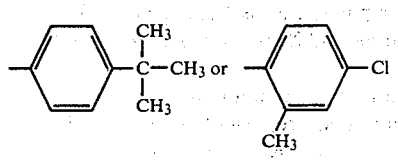

or α-naphthyl.

The compounds of the present invention are prepared for example, as follows:

A compound represented by the formula:

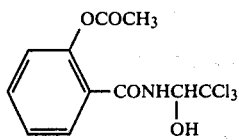

is reacted with a halogenating agent to form a compound represented by the formula:

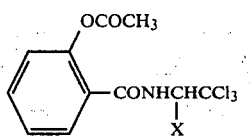

wherein X represents halogen, and then the resulting compound is reacted with a compound represented by the formula:

$$R_2OH \qquad (IV)$$

wherein $R_2$ has the same meaning as above, to obtain a compound represented by formula (I) wherein $R_1$ is acetyl:

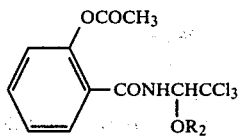

When a compound of formula (V) is hydrolyzed in the presence of an acid catalyst, a compound of formula (I) wherein $R_1$ is hydrogen:

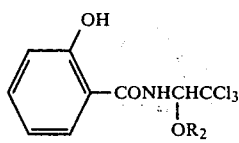

can be obtained.

A compound represented by formula (I) wherein $R_1$ is lower alkylcarbonyl, lower alkoxycarbonyl, phenoxycarbonyl or lower alkylsulfonyl can be obtained by reacting a compound represented by formula (VI) with an acid halide of the formula:

$$R'_1Cl \qquad (VII)$$

wherein $R'_1$ is lower alkylcarbonyl, lower alkoxycarbonyl, phenoxycarbonyl or lower alkylsulfonyl in the presence of a base. A compound represented by formula (I) wherein $R_1$ is lower alkylcarbamoyl can be obtained by reacting an isocyanic acid ester of the formula:

$$R_3NCO \qquad (VIII)$$

wherein $R_3$ represents lower alkyl with a compound of formula (VI) in the presence of a base. The compound represented by formula (II) used as a starting material can be prepared by reacting o-acetylsalicylamide with chloral.

The typical compounds of the present invention prepared by the procedures mentioned above are shown in Table 1.

TABLE 1

| Compound No. | R₁ | R₂ | Melting Point |
|---|---|---|---|
| 1 | H | ⟨⟩—CH₃ | 126–127° C. |
| 2 | H | 2,3-(CH₃)₂-phenyl | 165–166° C. |
| 3 | H | 2,6-(CH₃)₂-phenyl | 107–108° C. |
| 4 | H | 3,5-(CH₃)₂-phenyl | 95–96° C. |
| 5 | H | 2,4,6-(CH₃)₃-phenyl | 160–161° C. |
| 6 | H | ⟨⟩—OCH₃ | 139–140° C. |
| 7 | H | 2-OCH₃-phenyl | 133–134° C. |
| 8 | H | ⟨⟩—COOCH₃ | 136–138° C. |
| 9 | H | ⟨⟩—Cl | 116–117° C. |

TABLE 1-continued $$\text{(I)} \quad \text{2-}(OR_1)\text{-C}_6H_4\text{-CONHCH(OR_2)CCl}_3$$

| Compound No. | $R_1$ | $R_2$ | Melting Point |
|---|---|---|---|
| 10 | H | 2-F-phenyl | 130–131° C. |
| 11 | H | 4-CN-phenyl | 72–74° C. |
| 12 | H | 3-NO₂-phenyl | 148–150° C. |
| 13 | H | 4-NO₂-phenyl | 74–76° C. |
| 14 | H | 2-COCH₃-phenyl | 124–126° C. |
| 15 | H | 4-Cl-3-CH₃-phenyl | 119–120° C. |
| 16 | H | 4-Cl-2-CH₃-phenyl | 108–109° C. |
| 17 | H | 2,6-(CH₃)₂-4-SCN-phenyl | 68–71° C. |
| 18 | —COCH₃ | 3-CH₃-phenyl | 152–153° C. |
| 19 | —COCH₃ | 4-CH₃-phenyl | 141–142° C. |
| 20 | —COCH₃ | 3,5-(CH₃)₂-phenyl | 133–134° C. |
| 21 | —COCH₃ | 2,5-(CH₃)₂-phenyl | 119–120° C. |
| 22 | —COCH₃ | 2,4-(CH₃)₂-phenyl | 108–110° C. |
| 23 | —COCH₃ | 2,3-(CH₃)₂-phenyl | 142–143° C. |
| 24 | —COCH₃ | 2,4,5-(CH₃)₃-phenyl | 130–131° C. |
| 25 | —COCH₃ | 3-OCH₃-phenyl | 102–103° C. |
| 26 | —COCH₃ | 3-Cl-phenyl | 156–157° C. |
| 27 | —COCH₃ | 3,4-Cl₂-phenyl | 142–143° C. |
| 28 | —COCH₃ | 3-F-phenyl | 157–158° C. |
| 29 | —COCH₃ | 4-NO₂-phenyl | 176–177.5° C. |
| 30 | —COCH₃ | 3-NO₂-phenyl | 183–184.5° C. |
| 31 | —COCH₃ | 3-SC₃H₇(n)-phenyl | 111–112° C. |
| 32 | —COCH₃ | 2-COOCH₃-phenyl | 125–126° C. |
| 33 | H | 2-Cl-phenyl | 129–130° C. |
| 34 | —COCH₃ | 4-CHO-3-CH₃O-phenyl | 142–143° C. |
| 35 | —COCH₃ | 4-NHCOCH₃-phenyl | 211–212° C. |
| 36 | —COCH₃ | 2-SCH₃-3-CH₃-phenyl | 120–121° C. |
| 37 | —COCH₃ | 4-Cl-3-CH₃-phenyl | 110–111° C. |
| 38 | —COCH₃ | 4-Cl-3-CH₃-phenyl | 135–136° C. |

TABLE 1-continued $$\text{structure: 2-OR}_1\text{-C}_6\text{H}_4\text{-CONHCHCCl}_3 \text{ with OR}_2 \text{ on the CH} \quad (I)$$

| Compound No. | R₁ | R₂ | Melting Point |
|---|---|---|---|
| 39 | —COCH₃ | 2-(COCH₃)-phenyl | 136–139° C. |
| 40 | —COCH₃ | 3-Cl-4-(SCH₃)-phenyl | 112–113° C. |
| 41 | —COCH₃ | 3-CH₃-4-(SOCH₃)-phenyl | 137–139° C. |
| 42 | —COCH₃ | 2,6-(CH₃)₂-4-SCN-phenyl | 134–136° C. |
| 43 | —COOCH₃ | phenyl | 105–106° C. |
| 44 | —COOC₂H₅ | phenyl | 132–133° C. |
| 45 | —SO₂CH₃ | phenyl | 193–195° C. |
| 46 | —COO-phenyl | phenyl | 110–111° C. |
| 47 | —COCH₃ | 2-Cl-phenyl | 143–144° C. |
| 48 | —CONHCH₃ | phenyl | 138–141° C. |
| 49 | —COCH₃ | 4-Cl-phenyl | 177–178° C. |
| 50 | H | naphthyl | 144–145° C. |
| 51 | —COCH₃ | naphthyl | 121–122° C. |
| 52 | —COCH₃ | naphthyl | 158–160° C. |
| 53 | —COCH₃ | 4-C(CH₃)₃-phenyl | 138–140° C. |
| 54 | H | 4-phenyl-phenyl | 132–135° C. |
| 55 | —COCH₃ | 3-CH₃O-phenyl | 84–85° C. |
| 56 | —COCH₃ | 4-SCH₃-phenyl | 118–119° C. |
| 57 | —COCH₃ | 4-CH(CH₃)₂-phenyl | 133–134° C. |
| 58 | H | 4-CH(CH₃)₂-phenyl | 142–143° C. |
| 59 | —COCH₃ | 4-OCH₃-phenyl | 121–123° C. |
| 60 | H | 3-CH₃-4-SO₂CH₃-phenyl | 155–156° C. |
| 61 | —COCH₃ | 3-CH₃-4-SO₂CH₃-phenyl | 152–153° C. |
| 62 | —COCH₃ | 4-SO₂CH₃-phenyl | 177–179° C. |
| 63 | H | 3-CH₃-phenyl | 125–126° C. |
| 64 | H | 3,5-(CH₃)₂-phenyl | 134–135° C. |
| 65 | —COCH₃ | 3,5-(CH₃)₂-phenyl | 127–128° C. |

For further illustration of methods of preparing the compounds of the present invention, the following examples are given, which by no means limit the present invention.

PREPARATION EXAMPLE 1

N-(1′-p-methylphenoxy-2′,2′,2′-trichloroethyl)-2-hydroxybenzamide (Compound No.1)

15.0 g of N-(1′,2′,2′,2′-tetrachloroethyl)-2-acetoxybenzamide and 5.65 g of p-cresol were dissolved in 250 ml of acetone. 5.3 g of triethylamine were added dropwise thereto at a temperature below 12° C. After effecting the reaction at room temperature for 30 minutes, the reaction mixture was poured into water. 15.2 g of white N-(1′-p-methylphenoxy-2′,2′,2′-trichloroethyl)-2-acetoxybenzamide were obtained. The compound was suspended in 300 ml of ethanol, then 3.6 ml of concentrated hydrochloric acid were added thereto and the reaction was carried out at −60°–70° C. for three hours. After cooling, the reaction mixture was poured into water to obtain 14.3 g of N-(1′-p-methylphenoxy-2′,2′,2′-trichloroethyl)-2-hydroxbenzamide as white crystals. M.p. 126°–127° C.

PREPARATION EXAMPLE 2

N-(1'-p-Chlorophenoxy-2',2',2'-trichloroethyl)-2-hydroxybenzamide (Compound No. 9)

4.8 g of p-chlorophenyl were dissolved in 150 ml of benzene. 0.8 of metallic sodium was added thereto and the reaction was carried out under heating for one hour. After cooling, 8.0 of N-(1',2',2',2'-tetrachloroethyl)-2-acetoxybenzamide were added thereto at a temperature below 10° C. The reaction was continued for one hour and the reaction mixture was poured into water. The benzene layer was separated out, washed with water and benzene was removed under reduced pressure to obtain 5.4 g of N-(1'-p-chlorophenoxy-2',2',2'-trichloroethyl)-2-acetoxybenzamide as white crystals. The compound thus obtained was suspended in 300 ml of ethanol, then 0.5 ml of concentrated hydrochloric acid was added thereto and the reaction was carried out at 60°–70° C. for three hours. After cooling, the reaction mixture was poured into a large amount of water to obtain 4.2 g of N-(1'-p-chlorophenoxy-2',2',2'-trichloroethyl)-2-hydroxybenzamide as white crystals.

Melting point: 116°–117° C.

PREPARATION EXAMPLE 3

N-(1'-2'',5''-dimethylphenoxy-2',2',2'-trichloroethyl)-2-acetoxybenzamide (Compound No. 21)

15.0 g of N-(1',2',2',2'-tetrachloroethyl)-2-acetoxybenzamide and 6.4 g of 2,5-dimethylphenyl were dissolved in 250 ml of acetone. 5.3 g of triethylamine were added dropwise thereto at a temperature of below 10° C. After the reaction was carried out for one hour, the reaction mixture was poured into water. The crystals which thus resulted were recrystallized from water-methanol to obtain 14.5 g of N-(1'-2'',5''-dimethylphenoxy-2',2',2'-trichloroethyl)-2-acetoxybenzamide as white crystals. Melting point: 119°–120° C.

PREPARATION EXAMPLE 4

N-(1'-3''-methyl-4''-methylthiophenoxy-2',2',2'-trichloroethyl)-2-acetoxybenzamide (Compound No. 36)

17.0 g of N-(1',2',2',2'-tetrachloroethyl)-2-acetoxybenzamide and 7.7 g of 3-methyl-4-(methylthio)-phenol were dissolved in 100 ml of acetone. 12 g of 20% aqueous NaOH solution were added dropwise thereto at a temperature below 20° C. After the reaction was carried out for one hour, the reaction mixture was poured into water. The crystals which thus resulted were recrystallized from n-hexane/benzene to obtain 18.4 of N-(1'-3''-methyl-4''-methylthiophenoxy-2',2',2'-trichloroethyl)-2-acetoxybenzamide as white crystals.

Melting point: 120°–121° C.

PREPARATION EXAMPLE 5

N-(1'-β-napthoxy-2',2',2'-trichloroethyl)-2-acetoxybenzamide (Compound No. 52)

8.5 g of N-(1',2',2',2'-tetrachloroethyl)-2-acetoxybenzamide and 3.6 g of β-naphthol were dissolved in 50 ml of acetone, and the temperature was maintained at 5°–15° C. by cooling in an ice-water bath. Then 4.5 ml of triethylamine were added dropwise and slowly to the solution under stirring. Then, the reaction was carried out at room temperature for about one hour and the reaction mixture was poured into water. The crystals which thus resulted were recrystallized from ethanol.

5.4 g of N-(1'-β-naphthoxy-2',2',2'-trichloroethyl)-2-acetoxybenzamide were obtained as white crystals. Melting point: 158°–160° C.

PREPARATION EXAMPLE 6

N-(1'-β-naphthoxy-2',2',2'-trichloroethyl)-2-hydroxybenzamide (Compound No. 50)

50 ml of ethanol and 1 ml of concentrated hydrochloric acid were added to 4.2 g of N-(1'-β-naphthoxy-2',2',2'-trichloroethyl)-2-acetoxybenzamide synthesized in Preparation Example 5. The whole was refluxed for about three hours. After cooling, the reaction mixture was poured into water and the resulting crystals were recrystallized from N-hexane/benzene (2:1) to obtain 2.0 g of N-(1'-β-naphthoxy-2',2',2'-trichloroethyl)-2-hydroxybenzamide as white crystals.

Melting point: 144°–145° C.

PREPARATION EXAMPLE 7

N-(1'-phenoxy-2',2',2'-trichloroethyl)-2-methylcarbamoyl-oxybenzamide (Compound No. 48)

10 g of N-(1'-phenoxy-2',2',2'-trichloroethyl)-2-hydroxybenzamide and 1.8 g of methyl isocyanate were dissolved in 150 mml of acetone. Two or three drops of triethylamine were added to the solution under stirring. After allowing to stand overnight, the reaction mixture was poured into water and the crystals which thus resulted were recrystallized from methanol to obtain 4.2 g of N-(1'-phenoxy-2',2',2'-trichloroethyl)-2-methylcarbamoyloxybenzamide as white crystals. Melting point: 138°–141° C.

PREPARATION EXAMPLE 8

N-(1'-phenoxy-2',2',2'-trichloroethyl)-2-phenoxycarbonyloxybenzamide (Compound No. 46):

10 g of N-(1'-phenoxy-2',2',2'-trichloroethyl)-2-hydroxybenzamide and 5.2 g of phenyl chlorocarbonate were dissolved in 200 ml of acetone and the solution was kept at a temperature below 10° C. with an ice-water bath. 3.3 g of triethylamine were added dropwise thereto under stirring and the reaction was continued at room temperature for a further period of three hours. The reaction mixture was poured into water and the resulting crystals were recrystallized from methanol to obtain 5.2 g of N-(1'-phenoxy-2',2',2'-trichloroethyl)-2-phenoxycarbonyloxybenzamide as which crystals.

Melting point: 110°–111° C.

The compounds of the present invention are used as agricultural or horticultural fungicides sometimes solely but usually in various types of formulations, with carriers or other adjuvants, such as emulsion, wettable powder, dusts, granules and micro granules in compliance with the intended purposes. In this case, the content of a compound of formula (I) in the formulations will usually be satisfactory if it is the same as that of the effective component in conventional formulations: namely, 0.5 to 95%, preferably 2 to 70%.

Both solid carriers and liquid carriers can be used. The solid carriers include clay, kaolin, talc, diatomaceous earth, silica, and calcium carbonate, and the liquid carriers include benzene, alcohols, acetone, xylene, methylnaphthalene, cyclohexanone, dimethylformamide, dimethylsulfoxide, animal or vegetable oils, fatty acids, fatty acid esters, and many kinds of surface active agents. Adjuvants other than carriers usually used for agricultural chemicals such as spreading agents, emulsifiers, wetting agents, dispersing agents and fixing agents can be properly mixed in order to assure the the desired effects. of The compounds of the present invention can be used in the form of blends with other herbicides, insecticides, acaricides, agricultural and horticultural fungicides, soil fungicides, soil stabilizers or fertilizers.

Further detailed formulation examples of the present invention will be illustrated below. The kinds of adjuvants and the mixing ratios should not be limited within the range of the examples but can be utilized in wider ranges for practical uses.

In the following examples, parts are given by weight.

Formulation Example 1

Dusts:

10 parts of compound No. 1 of the present invention [N-(1'-p-methylphenoxy-2',2',2'-trichloroethyl)-2-hydroxybenzamide], 41 parts of talc and 49 parts of clay were mixed together and pulverized to obtain a dust.

Formulation Example 2

Wettable powders:

80 parts of compound No. 9 [N-(1'-p-chlorophenoxy-2',2',2'-trichloroethyl)-2-hydroxybenzamide)] of the present invention, 15 parts of kaolin, 3 parts of a sodium higher alkyl sulfate and 2 parts of a sodium polyacrylate were mixed together and pulverized to obtain a wettable powder.

Formulation Example 3

Granules:

3 parts of compound No. 30 [N-(1'-m-nitrophenoxy-2',2',2'-trichloroethyl)-2-acetoxybenzamide] of the present invention, 35 parts of diatomaceous earth, 23 parts of bentonite, 37 parts of talc and 2 parts of a disintegrator were mixed together and 18 parts of water were added thereto to moisten the mixture homogeneously. Then, the mixture was extruded through an injection molding machine to obtain granules, which were then dried, treated in a crusher and regranulated by means of a granulator to obtain granules having a particle size of 0.6 to 1 mm.

Formulation Example 4

Micro granules:

5 parts of compound No. 48 [N-(1'-phenoxy-2',2',2'-trichloroethyl)-2-methylcarbamoyloxybenzamide] of the present invention were homogeneously mixed with 6 parts of bentonite and 9 parts of clay to make a concentrated powder mixture.

Separately, 80 parts of non-absorbent coarse mineral powder of 105 to 74 microns were placed in a proper mixing machine into which 20 parts of water were added under rotation to moisten the powder and then the above mentioned concentrated powder mixture was added thereto to coat the same. The products were dried to obtain micro granules.

Formulation Example 5

Emulsion:

20 parts of compound No. 51 [N-(1'-β-naphthoxy-2',2',2'-trichloroethyl)-2-hydroxybenzamide] were dissolved in 63 parts of xylene, into which 17 parts of a mixture of an alkylphenol-ethylene oxide condensate and a calcium alkylbenzenesulfonate (8:2) were mixed and dissolved to obtain an emulsion. The emulsion is to be used after dilution with water. When the composition in the form of a wettable powder, a water-soluble concentration or an emulsifiable concentration is practically applied to fungi which harm agricultural and horticultural plants or crops, it may preferably be diluted with water so that the present compounds are contained in an amount of about 25–8000 ppm, preferably 50–2000 ppm. In the form of a dust, pellets or granules, the present compound is used in an amount of 0.30 kg–1 kg/10 ares.

Although the compounds of the present invention can be used for soil treatment as they are, they are usually formulated as mentioned above. The quantity of the compounds of the present invention usable for the purpose of soil treatment varies depending on kind of the compounds used, the method of use and formulations, and is difficult to determine this quantity generally. However, they are used in an amount of usually 0.2 to 8 kg/10 are, preferably 0.2 to 6 kg/10 are, in the case of overall soil treatment; about 0.5 to 6 kg/10 are, preferably 1 to 5 kg/10 are, in the case of furrow treatment; and 0.1 to 2 g/plant, preferably 0.3 to 0.7 g/plant for treating planting holes.

The advantageous effects of the present invention will be shown by the following experimental results:

Test Example 1

Test on prevention of chinese cabbage clubroot:

An unglazed pot of 15 cm diameter was filled with soil infected by the pathogenic fungi of said disease (*Plasmodiophora brassicae*). The soil was mixed thoroughly with a 10% dust of the compositions of the present invention prepared by the same procedure as in Formulation Example 1 in an amount of 2 g in each pot. Thereafter, 15 seeds of chinese cabbage (variety: Taibyo 60-nichi) were sowed per pot.

The pot was buried in the field to allow the plant to be attacked by the pathogen.

A dust containing 20% of PCNB (active ingredient: pentachloronitrobenzene) was used as a control and tested in the same procedure as mentioned above.

4 weeks after sowing, the chinese cabbages were taken up and the degree of the attack by the fungus was observed.

"Percentage of healthy seedlings" was calculated as follows:

Percentage of healthy seedlings = $\dfrac{\text{number of healthy plants in each pot}}{\text{number of observed plants in each pot}} \times 100$ The results are shown in Table 2.

TABLE 2

| Compound No. | Active Component Quantity (per Pot) | Percentage of healthy seedlings | Phytotoxicity |
|---|---|---|---|
| 1 | 0.1 g | 100% | None |
| 2 | 0.1 g | 100 | None |
| 3 | 0.1 g | 98 | None |
| 4 | 0.1 g | 100 | None |
| 5 | 0.1 g | 92 | None |
| 6 | 0.1 g | 100 | None |
| 7 | 0.1 g | 80 | None |
| 8 | 0.1 g | 93 | None |
| 9 | 0.1 g | 100 | None |
| 10 | 0.1 g | 100 | None |
| 11 | 0.1 g | 90 | None |
| 12 | 0.1 g | 86 | None |
| 13 | 0.1 g | 88 | None |
| 14 | 0.1 g | 100 | None |
| 15 | 0.1 g | 85 | None |
| 16 | 0.1 g | 100 | None |

TABLE 2-continued

| Compound No. | Active Component Quantity (per Pot) | Percentage of healthy seedlings | Phytotoxicity |
|---|---|---|---|
| 17 | 0.1 g | 92 | None |
| 18 | 0.1 g | 100 | None |
| 19 | 0.1 g | 83 | None |
| 20 | 0.1 g | 97 | None |
| 21 | 0.1 g | 100 | None |
| 22 | 0.1 g | 84 | None |
| 23 | 0.1 g | 91 | None |
| 24 | 0.1 g | 93 | None |
| 25 | 0.1 g | 94 | None |
| 26 | 0.1 g | 100 | None |
| 27 | 0.1 g | 85 | None |
| 28 | 0.1 g | 100 | None |
| 29 | 0.1 g | 83 | None |
| 30 | 0.1 g | 90 | None |
| 31 | 0.1 g | 95 | None |
| 32 | 0.1 g | 89 | None |
| 33 | 0.1 g | 97% | None |
| 34 | 0.1 g | 63 | None |
| 35 | 0.1 g | 70 | None |
| 36 | 0.1 g | 100 | None |
| 37 | 0.1 g | 96 | None |
| 38 | 0.1 g | 100 | None |
| 39 | 0.1 g | 100 | None |
| 40 | 0.1 g | 78 | None |
| 41 | 0.1 g | 80 | None |
| 42 | 0.1 g | 83 | None |
| 43 | 0.1 g | 87 | None |
| 44 | 0.1 g | 86 | None |
| 45 | 0.1 g | 53 | None |
| 46 | 0.1 g | 95 | None |
| 47 | 0.1 g | 95 | None |
| 48 | 0.1 g | 85 | None |
| 49 | 0.1 g | 80 | None |
| 50 | 0.1 g | 100 | None |
| 51 | 0.1 g | 100 | None |
| 52 | 0.1 g | 87 | None |
| 53 | 0.1 g | 100 | None |
| 54 | 0.1 g | 95 | None |
| 55 | 0.1 g | 100 | None |
| 56 | 0.1 g | 100 | None |
| 57 | 0.1 g | 88 | None |
| 58 | 0.1 g | 100 | None |
| 59 | 0.1 g | 92 | None |
| 60 | 0.1 g | 90 | None |
| 61 | 0.1 g | 80 | None |
| 62 | 0.1 g | 90 | None |
| 63 | 0.1 g | 100 | None |
| 64 | 0.1 g | 97 | None |
| 65 | 0.1 g | 95 | None |
| Dust containing 20% PCNB | 0.1 g | 80 | None |
| Blank | — | 3 | — |

What we claim is:

1. A compound represented by the formula:

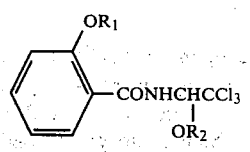

(I)

wherein $R_1$ is hydrogen, lower alkyl carbonyl, lower alkoxy carbonyl, phenoxy carbonyl, lower alkyl sulfonyl or lower alkyl carbamoyl, $R_2$ is phenyl; phenyl substituted by one or more members selected from the group consisting of lower alkyl, lower alkoxy, lower alkylthio, lower alkoxy carbonyl, halogen, formyl, cyano, thiocyano, nitro, lower alkyl sulfinyl, lower alkyl sulfonyl, lower alkyl carbonyl, acetylamino or phenyl; or naphthyl, with the proviso that when $R_1$ is hydrogen or lower alkyl carbonyl, $R_2$ is the said substituted phenyl or naphthyl.

2. The compound according to claim 1 wherein $R_1$ is hydrogen and $R_2$ is substituted phenyl represented by the formula:

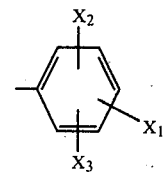

wherein $X_1$ is alkyl having 1-4 carbon atoms, methoxy, methoxycarbonyl, halogen, cyano, nitro, acetyl, thiocyano or phenyl, and $X_2$ is hydrogen or alkyl having 1-3 carbon atoms and $X_3$ is hydrogen or methyl; or $\beta$-naphthyl.

3. The compound according to claim 2 wherein $R_1$ is hydrogen and $R_2$ is substituted phenyl represented by the formula:

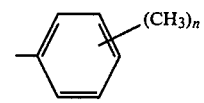

wherein n is an integer of 1 of 3;

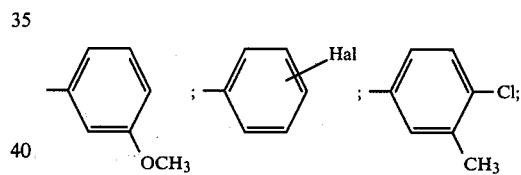

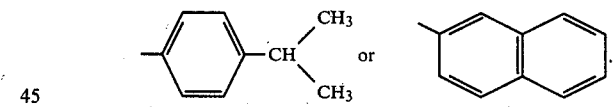

4. The compound according to claim 3 wherein $R_1$ is hydrogen and $R_2$ is

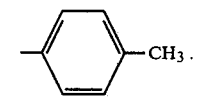

5. The compound according to claim 3 wherein $R_1$ is hydrogen and $R_2$ is

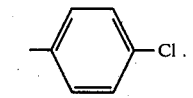

6. The compound according to claim 1 wherein $R_1$ is acetyl and $R_2$ is substituted phenyl represented by the formula:

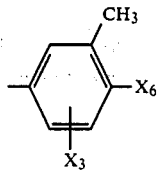

wherein $X_6$ is hydrogen, methylthio or chloro, $X_3$ is hydrogen or methyl which is in m- or p-position to the methyl on the phenyl nucleus, with the proviso that when $X_3$ is methyl, $X_6$ is hydrogen; substituted phenyl represented by the formula:

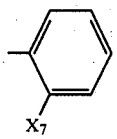

wherein $X_7$ is methyl, chloro, acetyl or methoxy; substituted phenyl represented by the formula:

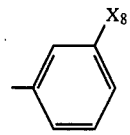

wherein $X_8$ is chloro, fluoro; substituted phenyl represented by the formula:

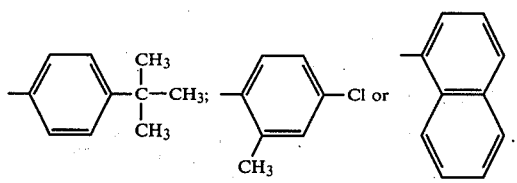

7. A fungicidal composition for agriculture and horticulture comprising 0.5 to 95% by weight of a compound of the formula:

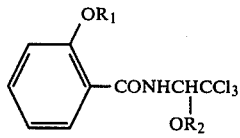

(I)

wherein $R_1$ is hydrogen; lower alkyl carbonyl, lower alkoxy carbonyl, phenoxy carbonyl, lower alkyl sulfonyl or lower alkyl carbonyl, $R_2$ is phenyl; phenyl substituted by one or more members selected from the groups consisting of lower alkyl, lower alkoxy, lower alkylthio, lower alkoxy carbonyl, halogen, formyl, cyano, thiocyano, nitro, lower alkyl sulfinyl, lower alkyl sulfonyl, lower alkyl carbonyl, acetylamino or phenyl; or naphthyl; with the proviso that when $R_1$ is hydrogen or lower alkyl carbonyl, $R_2$ is the said substituted phenyl or naphthyl, and 99.5 to 5% by weight of one or more adjuvants.

8. The composition according to claim 7 wherein $R_1$ is hydrogen and $R_2$ is substituted phenyl represented by the formula:

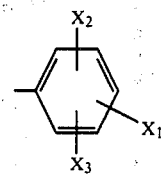

wherein $X_1$ is alkyl having 1–4 carbon atoms, methoxy, methoxycarbonyl, halogen, cyano, nitro, acetyl, thiocyano or phenyl, $X_2$ is hydrogen or alkyl having 1–3 carbon atoms and $X_3$ is hydrogen or methyl; or β-naphthyl.

9. The composition according to claim 8 wherein $R_1$ is hydrogen and $R_2$ is substituted phenyl represented by the formula:

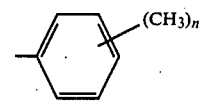

wherein n is an integer of 1 to 3;

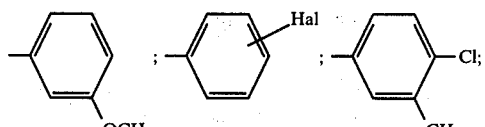

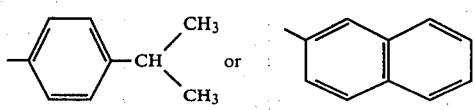

10. The composition according to claim 7 wherein $R_1$ is acetyl and $R_2$ is substituted phenyl represented by the formula:

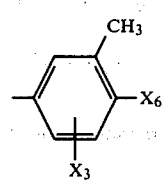

wherein $X_6$ is hydrogen, methylthio or chloro, $X_3$ is hydrogen or methyl which is in m- or p-position to the methyl on the phenyl nucleus, with the proviso that when $X_3$ is methyl, $X_6$ is hydrogen, substituted phenyl represented by the formula:

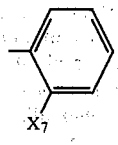

wherein $X_7$ is methyl, chloro, acetyl or methoxy;

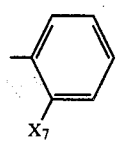

wherein $X_8$ is chloro, fluoro, substituted phenyl represented by the formula:

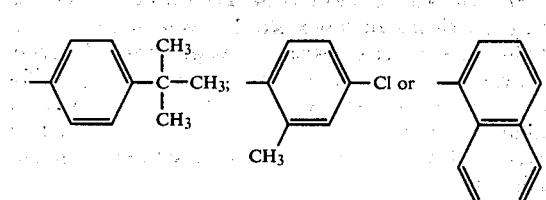

11. A method for preventing diseases of plant caused by fungi comprising applying to said fungi a fungicidally effective amount of a compound represented by the formula:

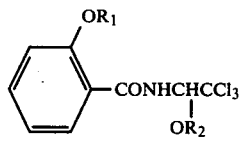

wherein $R_1$ is hydrogen, lower alkyl carbonyl, lower alkoxy carbonyl, phenoxy carbonyl, lower alkyl sulfonyl or lower alkyl carbamoyl, $R_2$ is phenyl; phenyl substituted by one or more members selected from the group consisting of lower alkyl, lower alkoxy, lower alkylthio, lower alkoxy carbonyl, halogen, formyl cyano, thiocyano, nitro, lower alkyl sulfinyl, lower alkyl sulfonyl, lower alkyl carbonyl, acetylamino or phenyl; or naphthyl, with the proviso that when $R_1$ is hydrogen or lower alkyl carbonyl, $R_2$ is said substituted phenyl or naphthyl.

12. The method according to claim 11 wherein $R_1$ is hydrogen and $R_2$ is substituted phenyl represented by the formula:

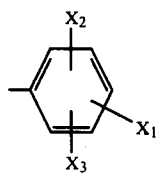

wherein $X_1$ is alkyl having 1–4 carbon atoms, methoxy, methoxycarbonyl, halogen, cyano, nitro, acetyl, thiocyano or phenyl, $X_2$ is hydrogen or alkyl having 1–3 carbon atoms and $X_3$ is hydrogen or methyl; or β-naphthyl.

13. The method according to claim 12 wherein $R_1$ is hydrogen and $R_2$ is substituted phenyl represented by the formula:

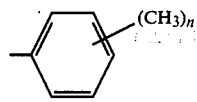

wherein n is an integer of 1 to 3;

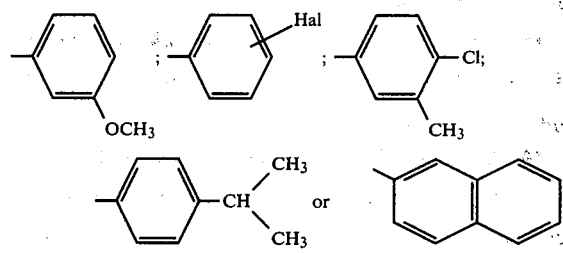

14. The method according to claim 11 wherein $R_1$ is acetyl and $R_2$ is substituted phenyl represented by the formula:

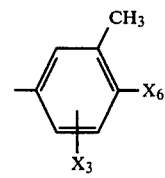

wherein $X_6$ is hydrogen, methylthio or chloro, $X_3$ is hydrogen or methyl which is in m- or p-position to methyl on the phenyl nucleus, with the proviso that when $X_3$ is methyl, $X_6$ is hydrogen; substituted phenyl represented by the formula:

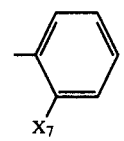

wherein $X_7$ is methyl, chloro, acetyl or methoxy;

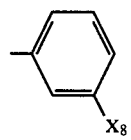

wherein $X_8$ is chloro, fluoro, substituted phenyl represented by the formula:

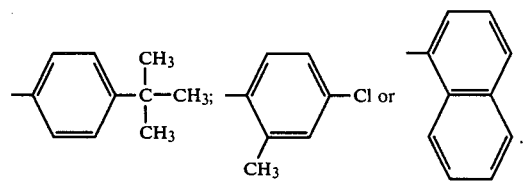

15. The method according to claim 11 wherein said disease caused by fungi is clubroot caused by *Plasmodiophora brassicae*.

16. The method according to claim 12 wherein said disease caused by fungi is clubroot caused by *Plasmodiophora brassicae*.

17. The method according to claim 13 wherein said disease is caused by fungi is clubroot caused by *Plasmodiophora brassicae*.

18. The method according to claim 14 wherein said disease caused by fungi is clubroot caused by *Plasmodiophora brassicae*.

19. A method for preventing or treating disease of plant caused by fungi which comprises treating soil containing the fungi with an effective amount of a compound represented by the formula:

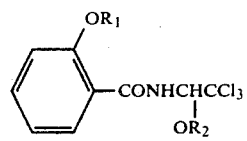

wherein $R_1$ is hydrogen, lower alkyl carbonyl, lower alkoxy carbonyl, phenoxy carbonyl, lower alkyl sulfonyl or lower alkyl carbamoyl $R_2$ is phenyl: phenyl substituted by one or more members selected from the group consisting of lower alkyl, lower alcoxy, lower alkylthiolower alcoxycarbanol, halogen, formyl, cyano, thiocyano, nitro, lower alkyl sulfinyl, lower alkyl sulfonyl, lower alkyl carbonyl, acetylamino or phenyl; or naphthyl, with the proviso that when $R_1$ is hydrogen or lower alkylcarbonyl, $R_2$ is the said substituted phenyl or naphthyl.

* * * * *